(12) United States Patent
Ling et al.

(10) Patent No.: US 11,492,580 B2
(45) Date of Patent: Nov. 8, 2022

(54) METHOD USING A THREE-DIMENSIONAL BIOPROCESSOR

(71) Applicants: Southwest Research Institute, San Antonio, TX (US); The Trustees of the University of Pennsylvania, Philadelphia, PA (US)

(72) Inventors: Jian Ling, Spring Branch, TX (US); Kreg A. Zimmern, San Antonio, TX (US); Michael C. Milone, Philadelphia, PA (US)

(73) Assignees: Southwest Research Institute, San Antonio, TX (US); The Trustees of the University of Pennsylvania, Philadelphia, PA (US)

(*) Notice: Subject to any disclaimer, the term of this patent is extended or adjusted under 35 U.S.C. 154(b) by 154 days.

(21) Appl. No.: 16/872,823

(22) Filed: May 12, 2020

(65) Prior Publication Data
US 2021/0355420 A1 Nov. 18, 2021

(51) Int. Cl.
*C12M 3/00* (2006.01)
*C12M 1/00* (2006.01)
*C12M 1/12* (2006.01)
*C12N 5/00* (2006.01)
*G01N 33/543* (2006.01)

(52) U.S. Cl.
CPC ............ *C12M 23/02* (2013.01); *C12M 23/20* (2013.01); *C12M 25/00* (2013.01); *C12N 5/0062* (2013.01); *G01N 33/54313* (2013.01)

(58) Field of Classification Search
CPC .......................... C12M 25/14; C12M 25/18
See application file for complete search history.

(56) References Cited

U.S. PATENT DOCUMENTS

| | | | |
|---|---|---|---|
| 4,247,434 A | 1/1981 | Vanderhoff | |
| 5,360,609 A | 11/1994 | Wellinghoff | |
| 5,443,950 A | 8/1995 | Naughton | |
| 5,516,691 A * | 5/1996 | Gerlach | ................ C12M 25/10 |
| | | | 435/297.1 |

(Continued)

FOREIGN PATENT DOCUMENTS

| CA | 2882108 A1 | 3/2014 |
|---|---|---|
| KR | 2013-0134080 A | 12/2013 |

(Continued)

OTHER PUBLICATIONS

Gordon, G. et la., "The Chemistry of Chlorine Dioxide," Progress in Inorganic Chemistry 15, pp. 201-286 (1972).

(Continued)

*Primary Examiner* — Nathan A Bowers
(74) *Attorney, Agent, or Firm* — Nixon Peabody LLP

(57) ABSTRACT

Described herein is a beads-free bioprocessor as an automated and cost-effective T cell processing and manufacturing platform. T cells are a core component in CAR T cell therapies for cancer treatment, but are difficult to manufacture to scale in clinically relevant quantities. The 3D bioprocessor provides an alternative device that is scalable, beads-free, easy-to-use, and cost-effective for using CAR T cell therapy in cancer immunotherapy. Besides CAR T cell application, this platform technology has potential for many other applications such as cancer cell isolation.

30 Claims, 6 Drawing Sheets

(56) References Cited

U.S. PATENT DOCUMENTS

| | | | |
|---|---|---|---|
| 5,631,300 A | 5/1997 | Wellinghoff | |
| 5,639,295 A | 6/1997 | Wellinghoff | |
| 5,650,446 A | 7/1997 | Wellinghoff | |
| 5,668,185 A | 9/1997 | Wellinghoff | |
| 5,695,814 A | 12/1997 | Wellinghoff | |
| 5,705,092 A | 1/1998 | Wellinghoff | |
| 5,707,739 A | 1/1998 | Wellinghoff | |
| 5,888,528 A | 3/1999 | Wellinghoff | |
| 5,914,120 A | 6/1999 | Wellinghoff | |
| 5,922,776 A | 7/1999 | Wellinghoff | |
| 6,046,243 A | 4/2000 | Wellinghoff | |
| 6,143,556 A * | 11/2000 | Trachtenberg | C12M 23/24 435/293.1 |
| 6,277,408 B1 | 8/2001 | Wellinghoff | |
| 6,605,304 B1 | 8/2003 | Wellinghoff | |
| 7,041,234 B2 | 5/2006 | Wellinghoff | |
| 7,094,360 B2 | 8/2006 | Wellinghoff | |
| 7,098,359 B2 | 8/2006 | Wellinghoff | |
| 7,108,801 B2 | 9/2006 | Wellinghoff | |
| 7,147,800 B2 | 12/2006 | Wellinghoff | |
| 7,238,831 B2 | 7/2007 | Wellinghoff | |
| 7,273,567 B1 | 9/2007 | Wellinghoff | |
| 8,007,823 B2 | 8/2011 | Favis | |
| 8,399,047 B2 | 3/2013 | Lahann | |
| 8,900,610 B2 | 12/2014 | Wellinghoff | |
| 8,961,892 B2 | 2/2015 | Hutter | |
| 9,364,579 B2 | 6/2016 | Wellinghoff | |
| 9,456,893 B2 | 10/2016 | Ling | |
| 9,512,393 B2 | 12/2016 | Kasuto | |
| 10,988,724 B2 | 4/2021 | Ling | |
| 2004/0062809 A1 | 4/2004 | Honiger | |
| 2005/0038492 A1 | 2/2005 | Mason | |
| 2005/0238683 A1 | 10/2005 | Adhikari | |
| 2006/0121005 A1 | 6/2006 | Berenson | |
| 2007/0178586 A1 | 8/2007 | Yang | |
| 2009/0041825 A1 | 12/2009 | Kotov | |
| 2010/0273667 A1 * | 10/2010 | Kotov | C12M 21/08 422/135 |
| 2012/0183987 A1 * | 7/2012 | Gevaert | G01N 33/5029 435/325 |
| 2012/0208265 A1 | 8/2012 | Partsch | |
| 2013/0030548 A1 | 1/2013 | Ling | |
| 2013/0344229 A1 | 12/2013 | Messersmith | |
| 2014/0328789 A1 * | 11/2014 | Auguste | A61K 31/785 521/149 |
| 2015/0087057 A1 | 3/2015 | Zink | |
| 2016/0200891 A1 | 7/2016 | Virgilio | |
| 2017/0081638 A1 | 3/2017 | Ma | |
| 2017/0321178 A1 | 11/2017 | Ling | |
| 2018/0104914 A1 * | 4/2018 | Kim | C04B 35/52 |
| 2020/0010826 A1 * | 1/2020 | Liberti | C12M 35/08 |
| 2021/0079333 A1 * | 3/2021 | Matsubayashi | C12M 21/08 |
| 2021/0340492 A1 * | 11/2021 | Hasselmann | G03F 7/027 |

FOREIGN PATENT DOCUMENTS

| | | |
|---|---|---|
| WO | WO 2008/140295 A1 | 11/2008 |
| WO | WO 2011/072393 A1 | 6/2011 |
| WO | WO 2013/036585 A1 | 4/2013 |
| WO | WO 2012/168295 A1 | 12/2013 |
| WO | WO 2014/037862 A1 | 3/2014 |
| WO | WO 2015/001321 A1 | 1/2015 |
| WO | WO 2017/049066 A1 | 3/2017 |
| WO | WO 2017/099712 A1 | 6/2017 |
| WO | WO 2018/005521 A1 | 1/2018 |
| WO | WO 2018/013797 A1 | 1/2018 |
| WO | WO 2018/075940 A1 | 4/2018 |
| WO | WO 2019/194842 A1 | 10/2019 |
| WO | WO 2020/068840 A1 | 4/2020 |

OTHER PUBLICATIONS

Looby, D. & Griffiths, J.B., "Fixed bed porous glass sphere (porosphere) bioreactors for animal cells," Cytotechnology 1, pp. 339-346 (1988).

Ma, P.X. and Choi, J-W., "Biodegradable Polymer Scaffolds with Well-Defined Internconnected Spherical Pore Network," Tissue Engineering, 7(1):23-33 (2001).

Chen, G. et al., "Scaffold Design for Tissue Engineering," Macromolecular Bioscience 2, pp. 67-77 (2002).

Ma, Z. et al., "Paraffin Spheres as Porogen to Fabricate Poly(L-Lactic Acid) Scaffolds with Improved Cytocompatibility for Cartilage Tissue Engineering," J. Biomed. Mater. Res. Part B: Appl. Biomater 67B, pp. 610-617 (2003).

Boland, E. et al., "In Vitro Cytotoxicity of a Low-shrinkage Polymerizable Liquid Crystal Resin Monomer," Journal of Biomedical Materials Research Part B, Applied Biomaterials, 79(1):1-6 (2006).

Wellinghoff, S. et al., "Advanced Dental Restorative Composites Utilizing Low Polymerization Shrinkage Liquid Crystalline Monomers," Physical Chemistry, pp. 479-485 (2006).

Zhang, J. et al., "Fabrication of Three Dimensional Polymeric Scaffolds with Spherical Pores," J. Mater. Sci. 41, pp. 1725-1731 (2006).

Nagrath, S. et al., "Isolation of rare circulating tumour cells in cancer patients by microchip technology," Nature, 450(7173):1235-1239 (2007).

Portner, R. et al., "Fixed Bed Reactors for the Cultivation of Mammalian Cells: Design, Performance, and Scale-Up," The Open Biotechnology Journal 1, pp. 41-46 (2007).

Elkasabi, Y. et al., "Towards Multipotent Coatings: Chemical Vapor Deposition and Biofunctionalization of Carbonyl-Substituted Copolymers," Macromolecular Rapid Communications, 29(11):855-870 (2008).

Provin, C. et al., "A Method for the Design of 3D Scaffolds for High-Density Cell Attachment and Determination of Optimum Perfusion Culture Conditions," Journal of Biomechanics 41, pp. 1436-1449 (2008).

Schop, D. et al., "Expansion of Mesenchymal Stem Cells Using a Microcarrier-based Cultivation System: Growth and Metabolism," Journal of Tissue Engineering and Regeneration Medicine 2L, pp. 126-135 (2008).

Sailon, A. et al., "A Novel Flow-Perfusion Bioreactor Supports 3D Dynamic Cell Culture," Journal of Biomedicine and Biotechnology 2009: 873816.

Yamada, S. et al., "Multi-sized Sphere Packing," (2009).

Frith, J. et al., "Dynamic Three-Dimensional Culture Methods Enhance Mesenchymal Stem Cell Properties and Increase Therapeutic Potential," Tissue Engineering Part C, Methods, 16(4):735-749 (2010).

Tan, C. et al., "Surface Engineering and Patterning Using Parylene for Biological Applications," Materials, 3(3):1803-1832 (2010).

Weber, C. et al., "Production Process for Stem Cell Based Therapeutic Implants: Expansion of the Production Cell Line and Cultivation of Encapsulated Cells," Advances in Biochemical Engineering Biotechnology 23, pp. 143-162 (2010).

Yourek, G. et al., "Shear Stress Induces Osteogenic Differentiation of Human Mesenchymal Stem Cells," Regenerative Medicine, 5(5):7131-7724 (2010).

Alves de Silva. M. et al., "Chondroenic Differentiation of Human Bone Marrow Mesenchymal Stem Cells in Chitosan-Based Scaffolds Using a Flow-perfusion Bioreactor," Journal of Tissue Engineering and Regenerative Medicine, 5(9):722-732 (2011).

Kalos, M. et al., "T Cells with Chimeric Antigen Receptors Have Potent Antitumor Effects and Can Establish Memory in Patients with Advanced Leukemia," Science Translational Medicine, (3):95 (2011).

Ko, H. et al., "One Step Immobilization of Peptides and Proteins by Using Modified Parylene with Formyl Groups," Biosensors and Bioelectronics, 30(1):56-60 (2011).

Mirro. R., "An Update on the Advantages of Fibra-Cel Disks for Cell Culture," Eppendorf, Application Note No. 313 (2011).

Porter, D.L. et al., "Chimeric antigen receptor-modified T cells in chronic lymphoid leukemia," The New England Journal of Medicine, 365(8):725-733 (2011).

Sobral, J.M., et al., "Three-dimensional Plotted Scaffolds with Controlled Pore Size Gradients: Effect of Scaffold Geometry on Mechanical Performance and Cell Seeding Efficiency," Acta Biomaterialia, 7(3):1009-1018 (2011).

(56) References Cited

OTHER PUBLICATIONS

Wen. Z. et al., "Repair Mechanisms of Bone Marrow Mesenchymal Stem Cells in Myocardial Infarction," Journal of Cellular and Molecular Medicine, 5(5):1032-1043 (2011).

Yang, S. et al., "Mussel-Inspired Encapsulation and Functionalization of Individual Yeast Cells," Journal of the American Chemical Society 133, pp. 2795-2797 (2011).

Higuera, G. et al., "The Physics of Tissue Formation with Mesenchymal Stem Cells," Trends in Biotechnology, 30(11):583-590 (2012).

Kim, J. et al., "Bioreactor Strategy in Bone Tissue Engineering: Pre-Culture and Osteogenic Differentiation Under Two Flow Configurations," Tissue Engineering: Part A, 18(21-22):2354-2364 (2012).

Kapyla et al., "Direct laser writing and geometrical analysis of scaffolds with designed pore architecture for three-dimensional cell culturing," Journal of Micromechanics and Microengineering, 22(11), (2012).

Brentjens, R.J. et al., "CD19-targeted T cells rapidly induce molecular remissions in adults with chemotherapy-refractory acute lymphoblastic leukemia," Science Translational Medicine, (5):177 (2013).

Gardel, L. et al., "A Novel Bidirectional Continuous Perfusion Bioreactor for the Culture of Large-sized Bone Tissue-engineered Constructs," Society for Biomaterials, Journal of Biomedical Materials Research B: Applied Biomaterials, 10 1B(8)1377-1386 (2013).

Glavaski-Joksimovic, A. et al., "Mesenchymal Stem Cells and Neuroregeneration in Parkinson's Disease," Experimental Neurology 247, pp. 25-38 (2013).

Grupp, S.A. et al., "Chimeric antigen receptor-modified T cells for acute lymphoid leukemia," The New England Journal of Medicine, 368(16):1509-1518 (2013).

Kochenderfer, J.N. & Rosenberg, S.A., "Treating B-cell cancer with T cells expressing anti-CD19 chimeric antigen receptors," Nat. Rev. Clin. Oncol., 10(5):267-276 (2013).

Yeatts, A. et al., "Bioreactors to Influence Stem Cell Fate: Augmentation of Mesenchymal Stem Cell Signaling Pathways via Dynamic Culture Systems," Biochimica et Biophysica Acta, 1830(2):2470-2480 (2013).

Choi, S. et al., "Alzheimer's Disease and Stem Cell Therapy," Experimental Neurobiology, 23(1):45-52 (2014).

Lechanteur, C. et al., "Large-Scale Clinical Expansion of Mesenchymal Stem Cells in the GMP-Compliant, Closed Automated Quantum Cell Expansion System: Comparison with Expansion in Traditional T-Flasks," Journal of Stem Cell Research & Therapy 04(08) (2014).

Malinauskas, M. et al., "3D Microporous Scaffolds Manufactured via Combination of Fused Filament Fabrication and Direct Laser Writing Ablation," Micromachines 5, pp. 839-858 (2014).

Maude, S.L. et al., "Chimeric antigen receptor T cells for sustained remissions in leukemia," The New England Journal of Medicine, 371(16):1507-1517 (2014).

Papadimitropoulos, A. et al., "Expansion of Human Mesenchymal Stromal Cells from Fresh Bone Marrow in a 3D Scaffold-Based System Under Direct Perfusion," PLOS ONE 9(7), (2014).

Whitford, W. et al., "Single-Use, Continuous Processing of Primary Stem Cells," BioProcess International, Therapy Processing, 12(3):26-33 (2014).

Wu, H. et al., "Mesenchymal Stem Cell-based Therapy for Type 1 Diabetes," Discovery Medicine, 17(93):139-143 (2014).

Kaiser, A. et al., "Towards a Commercial Process for the Manufacture of Genetically Modified T Cells for Therapy," Cancer Gene Therapy 22, pp. 72-78 (2015).

Kumar, A. et al, "Large Scale Industrialized Cell Expansion Producing the Critical Raw Material for Biofabrication Processes," Biofabrication, 7)4):044103 (2015).

Rapoport, A.P. et al., "NY-ESO-1-specific TCR-engineered T cells mediate sustained antigen-specific antitumor effects in myeloma," Nat. Med., 21(8):914-921 (2015).

Arifin, M. et al., "Ultraviolet/Ozone (UV/O3) Treated Polystyrene (PS) Microcarriers for Animal Cell Culture," Journal of Chemical Technology and Biotechnology, 91(10):2607-2619 (2015).

Vitale, A. et al., "Frontal Conversion and Uniformity in 3D Printing by Photopolymerisation," Materials 9(760), (2016).

Han, Y. et al., "High-Performance Nano-Photoinitiators with Improved Safety for 3D Printing," ACS Applied Materials and interfaces, 9(38):32418-32423 (2017).

Kumar, A. et al., "Human Mesenchymal Stem Cells Expansion on Three-Dimensional (3D) Printed Poly-Styrene (PS) Scaffolds in a Perfusion Bioreactor," Science Direct 65, pp. 115-120 (2017).

Kwon, T. et al., "Microfluidic Cell Retention Device for Perfusion of Mammalian Suspension Culture," Scientific Reports 7:6703 (2017).

Ligon, S. et al., "Polymers for 3D Printing and Customized Additive Manufacturing," Chemical Reviews, 17(15): 10212-10290 (2017).

Cheung, A. et al., "Scaffolds That Mimic Antigen-Presenting Cells Enable Ex Vivo Expansion of Primary T Cells," Nature Biotechnology (36)2 (2018).

Fenge, C. et al., "Sartorius Stedim Biotech," Large-Scale Perfusion and Concentrated Fed-Batch Operation of BIOSTAT STR Single-Use Bioreactor (2018).

Van Den Driesche, S. et al., "3D Printing Solutions for Microfluidic Chip-to-World Connections," Micromachines 9(71), (2018).

Caicedo-Carvajal, C.E., "3D Perfusion Bioreactor: The Cumulative Advantages of 3D Scaffold Geometry and Perfusion for Scale-up Processes: 3D Biotek," Technology Center of NJ.

"Dynabeads Human T-Activator CD3/CD28 for T Cell Expansion and Activation," Web page, URL: https://www.thermofisher.com/order/catalog/product/11161D, Retrieved from the Internet on Aug. 27, 2020 (5 pages).

General Electric Wave Bioreactor Systems, Cell Culture Procedures, Web pae, URL: https://www.gelifesciences.com/wave, Retrieved from the Internet on Aug. 27, 2020 (52 pages).

"Specialty Coating Systems Parylene Properties," Web page, URL: https://scscoatings.com/docs/brochures/parylene_properties.pdf, Retrieved from the Internet of Aug. 27, 2020 (12 pages).

International Search Report and Written Opinion in International Application No. PCT/US2021/031361, dated Aug. 27, 2021 (12 pages).

Dong, Y. et al., "Review Microfluidics and Circulating Tumor Cells," The Journal of Molecular Diagnostics, 15(2):149-157 (Jan. 1, 2013).

Zhang, D. Y. et al., "Activation and expansion of human T cells using artificial antigen-presenting cell scaffolds," Nature Protocols, 15(3):773-798, (Jan. 13, 2020).

\* cited by examiner

METHOD USING A THREE-DIMENSIONAL BIOPROCESSOR

STATEMENT REGARDING FEDERALLY SPONSORED RESEARCH OR DEVELOPMENT

This invention was made with government support under Grant No. 70NANB17H002 awarded by National Institute of Standards and Technology. The United States government has certain rights in the invention.

FIELD OF INVENTION

The present disclosure relates to the design, fabrication, and applications of a 3D bioprocessor for cell processing.

BACKGROUND

Cancer immunotherapy has come to symbolize the most recent phase of the biotechnology revolution in medicine. In 2017, FDA approved two CAR T cell based immunotherapies. In 2019, an estimated 412 clinical trials are ongoing worldwide in the field of CAR T-cell therapy. Cancer immunotherapy uses a patient's own immune system to treat cancer. One of the most exciting immunotherapy approaches uses artificial immunoreceptors, termed chimeric antigen receptors (CARs). CARs allow for synthetic control of the antigenic specificity of T cells.

A typical CAR T-cell therapy process is one in which T lymphocytes are collected from a patient's own blood and are genetically engineered to produce a special receptor CAR on their surface so that the T cells are able to recognize and attack cancer cells. The engineered CAR T cells are grown in the laboratory and expanded to billions of numbers, and then injected back to the patient to kill cancer cells.

Using T cells that are engineered to express a CAR targeting, the B-lymphocyte antigen CD19, a greater than 80% complete response rate and 60% overall survival at one year can be achieved in patients with acute lymphoblastic leukemia (ALL). Without CAR T therapy, these patients have an expected median survival of less than six months. This approach has also achieved durable complete responses in patients with other B-lineage hematologic malignancies including chronic lymphocytic leukemia (CLL), non-Hodgkin lymphoma (NHL) and multiple myeloma (MM) that affect more than 100,000 individuals in the U.S. alone as shown in Table 1 below. Currently, the approved engineered T cell therapies, such as tisagenlecleucel and axicabtagene ciloleucel, are autologous therapies where a single product is made for each patient using their own T cells as shown in FIG. 1.

TABLE 1

| Incidence rate and deaths of cancers where ACT has shown clinical activity | | |
|---|---|---|
| Cancer | US incidence | US deaths |
| Acute lymphoblastic leukemia (ALL) | 6,250 | 1,450 |
| Chronic lymphocytic leukemia (CLL) | 14,620 | 4,650 |
| Non-Hodgkin Lymphoma (NHL) | 71,850 | 19,790 |
| Multiple Myeloma | 26, R50 | 11,240 |

With the success of CAR T-cell therapy, the next question is how to make it safer and cost-efficient. The current T-cell engineering process is still generally based on using magnetic beads to incubate together with T-cells. The magnetic beads are coated with CD3 and CD28 on their surface to act as the antigens to activate the T-cells so they can proliferate. The micro-beads suspended in cell culture medium with T-cells provide a relatively large surface area for T-cells to contact and temporarily bind to CD3 and CD28 and then activate. After T-cells are grown to a certain density, the T-cells and magnetic beads are moved into a relatively large bioprocessor to continue the process of stimulation and expansion. The process is repeated multiple times to grow relatively large numbers of T-cells. At harvesting, the T cells have to be separated from the beads using a magnetic separator. Accordingly, the current T-cell expansion process generally relies upon magnetic beads, multi-stage processing, and manual interactions, which is not cost-effective. In addition, it is an open system, which can easily introduce contaminations and make it relatively more expensive to meet good manufacturing process (GMP) requirements.

The current manufacturing approaches, largely developed in academic medical centers, use a mixture of commercial products originally developed for other purposes (e.g., hematopoietic stem cells for transplantation). These devices have been adapted for use in T cell manufacturing and require significant process engineering to generate a congruent manufacturing process. Magnetic microbead-based ACT manufacturing has been successfully scaled into cGMP, processes. However, the effectiveness of this manufacturing platform is significantly reduced in leukemia patients, where the leukemic cell frequencies vastly exceed T cell frequencies. While manufacturing failure data has not been published in the most reported studies to date, observations of the inventors demonstrate that ~15-20% of patients with CLL cannot meet the target cell dose due to manufacturing failures. This may be attributable to the immunosuppressive effects of the leukemia cells. In addition to ex-vivo T cell expansion failures, products that are contaminated by non-T cells introduce additional cost and safety concerns. Non-T cell contamination also necessitates greater viral vector quantities to achieve target gene transfer and increases the cost of manufacturing. Genetically modifying non-T cells also introduce potential safety concerns. In particular, introducing a CD19-specific CAR into ALL cells has been associated with at least one disease relapse. This was due to CD19 antigen loss that appeared to be the result of CAR interactions with CD19, limiting its leukemic cell expression.

As shown in FIG. 2, current manufacturing generally requires multiple manual steps to produce a product. This leads to significant labor costs along with challenges to hiring and training the required staff. With the proposed platform, peripheral blood mononuclear cells (PBMCs), including T cells, B cells, NK cells, and monocytes, are isolated from a patient's blood via apheresis, and incubated with magnetic microbeads bearing agonist antibodies to CD3 and CD28 molecules in a traditional cell culture T-flask. The T cells in PBMCs, after colliding with the CD3/CD28 coated microbeads, are activated for expansion. Then the T cells are transduced with lentiviral vectors in the flask so they can express CAR on their surface to target cancer cells. After activation and transduction, the T-cells are moved into a large bioprocessor bag for further expansion. Finally, the T-cells are isolated from the microbeads during harvesting.

Efficient manufacturing approaches that reduce costs and allow for easy out-scaling is essential to meet the manufacturing needs to deliver these complex autologous CAR-T therapies world-wide. Described herein is a low cost, easy to manufacture, easy-to-use, and single-use 3D bioprocessor for cell processing in cell and gene therapy. This provides a high surface-to-volume ratio fixed-bed with adjustable structural parameters and scalability. The described 3D bioprocessor can also be applied for scale-up of allogenic CAR-T cell therapies. Furthermore, the 3D bioprocessor can be used for cell separation, isolation, and purification.

SUMMARY OF INVENTION

According to one method, one supplies a 3D bioprocessor including a plurality of spheres and a plurality of rods interconnecting the plurality of spheres, provides a coating on the bioprocessor surface area, and then provides a protein to attach to the coating, followed by providing one or more biotinylated antibodies immobilized on the protein. By flowing cells through the bioprocessor, the cells bind to the one or more biotinylated antibodies. In other embodiments, the cells can include T-cells, wherein receptors of the T-cells bind to the one or more biotinylated antibodies and are activated and further include exposing the activated T-cells to a perfusion media containing a signaling molecule to promote T-cell expansion. In other embodiments, the coating is a protein coating. In other embodiments, the protein includes a tetrameric protein. In other embodiments, the tetrameric protein includes avidin or streptavidin. In other embodiments, the one or more biotinylated antibody is one or more of anti-CD3 antibody, anti-CD28 antibody, and anti-CD2 antibody. In other embodiments, the signaling molecule includes a cytokine signaling molecule. In other embodiments, the 3D bioprocessor is formed from a material that has a Tensile Modulus of at least 0.01 GPa. In other embodiments, the 3D bioprocessor is formed from a material that is biocompatible. In other embodiments, the 3D bioprocessor is formed from a material not susceptible to hydrolysis during cell cultivation such that the amount of hydrolysis does not exceed 5.0% by weight of the material present. In other embodiments, the diameter of the spherical beads is from about 10 µm to about 10 mm. In other embodiments, the diameter of the spherical beads is from about 1 mm to about 3 mm. In other embodiments, the length of the cylindrical rods is from about 0.1 µm to about 10 mm. In other embodiments, the length of the cylindrical rods is from about 100 µm to about 3 mm. In other embodiments, the plurality of spheres and the plurality of rods are organized in one or more layers. In other embodiments, the one or more layers includes at least two layers, with each layer offset from an adjacent layer.

Also described herein is a quantity of T cells made by a method where one supplies the aforementioned 3D bioprocessor including a plurality of spheres and a plurality of rods interconnecting the plurality of spheres, provides a coating on the bioprocessor surface area, and then providing a protein to attach to the coating, followed by providing one or more biotinylated antibodies immobilized on the protein. By flowing cells through said bioprocessor, the cells bind to the one or more biotinylated antibodies.

Described herein is an apparatus, including a plurality of spheres and a plurality of rods interconnecting the plurality of spheres, wherein the diameter of the spherical beads is from about 10 µm to about 10 mm, the length of the cylindrical rods is from about 0.1 µm to about 10 mm, the plurality of spheres and the plurality of rods are organized in two or more layers, with each layer offset from an adjacent layer. In other embodiments, the diameter of the spherical beads is from about 1 mm to about 3 mm and the length of the cylindrical rods is from about 100 µm to about 3 mm. In other embodiments, the protein coating on the surface of the apparatus. In other embodiments, one or more biotinylated antibodies is attached to the protein coating. In other embodiments, the one or more biotinylated is one of anti CD3 antibody, anti-CD28 antibody, and anti-CD2 antibody.

The above summary is not intended to represent each embodiment or every aspect of the present invention. Additional features and benefits of the present invention are apparent from the detailed description and figures set forth below

DETAILED DESCRIPTION

Figure 1:
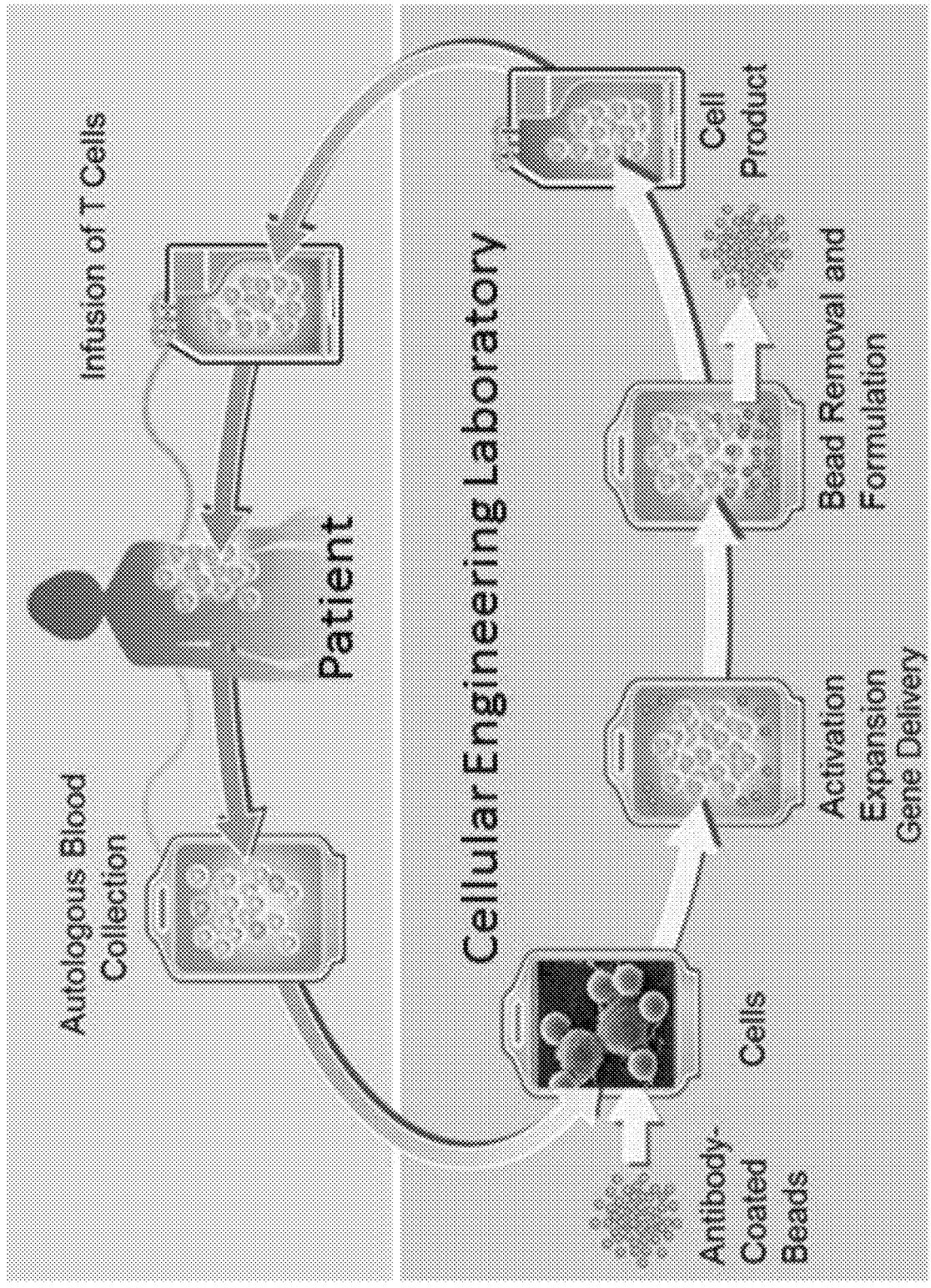
FIG. 1. Depicted is a typical process of CAR T-cell therapy for leukemia.
Figure 2:
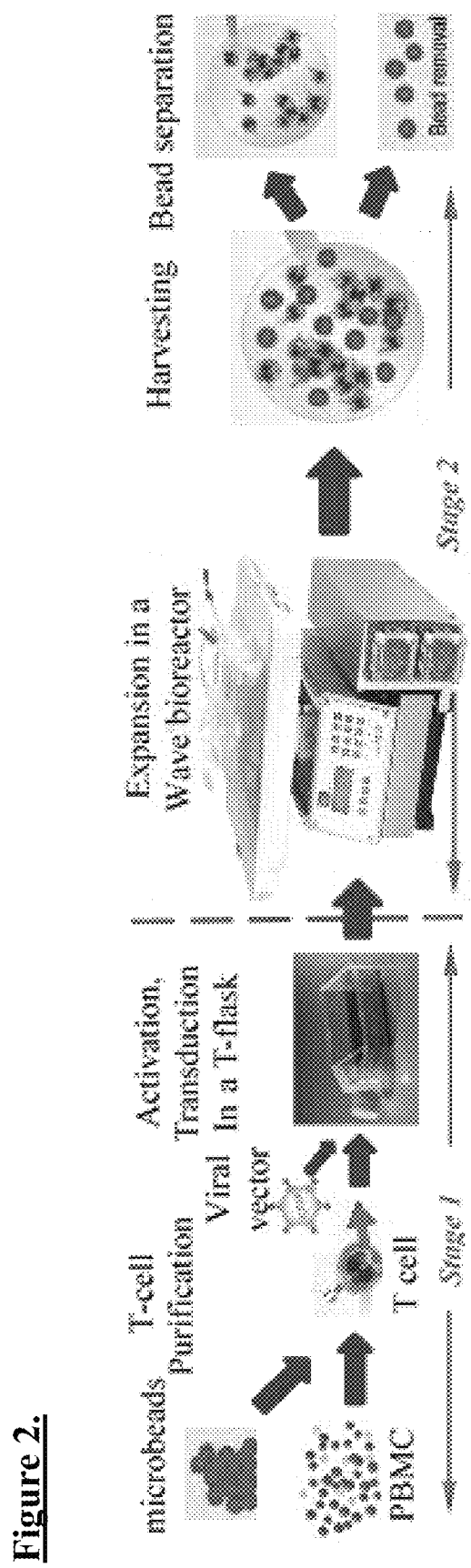
FIG. 2. Depicted is a representative conventional ex vivo T cell expansion process: Stage 1 (purification, activation, transduction), and Stage 2 (proliferation, harvesting). Disadvantages: 1) requires magnetic beads, 2) lacks of automation, 3) open system, 4) non-T cell contamination, and 5) lacks efficient use of expensive viral vectors and other reagents.

The current manufacturing methods produce engineering T cells under an open process, resulting in not only significant labor costs, but also GMP facility costs. Because cells as a living drug cannot be terminally sterilized like small molecule drugs, high cost ISO5 or Class 100 clean rooms are required during the entire manufacturing process to prevent or inhibit contamination. Automating T-cell manufacturing is an active area of development with a few commercial products that have built upon bead-based technologies. These are beginning to hit the market, however the success of these systems is undetermined.

Other challenges in CAR T-cell manufacturing are the problems related to using magnetic microbeads. First, the monocytes in PBMCs can uptake the microbeads and cause variability in T cell production. PBMCs containing a high percentage of monocytes are often not suitable for direct use in the above manufacturing process. Second, the magnetic de-beading process and downstream qualification steps further increase the operator time and cost. Third, there are only two types of magnetic beads commonly used in industry with one type only available for research, leaving a single source of microbeads for CAR T cell manufacturers. This supply restriction creates long lead times for manufacturing. Some new biodegradable beads are now available to activate T cells, however, they are not used commercially yet. In summary, the challenge of manufacturing consistent and cost-effective T cell based therapies significantly limits the number of patients that can benefit from this highly effective cancer therapy.

This invention discloses a low cost, easy to manufacture, easy-to-use, and single-use 3D bioprocess for cell processing in cell and gene therapy. This bioprocess provides a high surface-to-volume ratio fixed-bed with adjustable structural parameters and scalability. Here, a plurality of spheres is interconnected by rods, in a fixed structure of substantial uniformity. These interconnected sphere-rod unit designs capture a variety of benefits of microbead approaches but obviate their disadvantages. Advantages include high surface area-to-volume ratio to increase reactivity between cells and the bioprocessor surfaces, preventing cellular uptake from being both larger than microbeads and a fixed structure. Unlike loose microbeads, the designs form a repeatable and non-random mesh structure. This provides a variety of substantial benefits, including ensuring consistency of bioprocess and hydrodynamic forces on cells, more uniform biochemical surface for protein, antibody binding, or contact for T cell activation.

According to one method, one supplies a 3D bioprocessor with a plurality of spheres and a plurality of rods interconnecting the plurality of spheres, thereafter providing a coating on the bioprocessor surface area, and then providing a protein attached to the coating. One can then provide one or more biotinylated antibodies immobilized on the protein, flowing cells through the bioprocessor, wherein the cells bind to the one or more biotinylated antibodies. The cells can be a mixed population of cells with antibodies specific for one of the population of cells. Whereas certain cells will flow through and not be captured by the bioprocessor, antibodies specific for one of the population of cells will capture the population, which is isolated, or separated from other population. The separated populations can be further analyzed.

In other variations, the method includes a 3D bioprocessor including a plurality of spheres and a plurality of rods interconnecting the plurality of spheres is supplied. One provides a coating on the bioprocessor surface area for cell expansion, provides a protein attached to said coating, attaches one or more biotinylated antibodies immobilized on said protein, and then flows cells through the bioprocessor to facilitate cells bind to the one or more biotinylated antibodies.

In other variations, the 3D bioprocessor includes a plurality of spheres with a plurality of rods interconnecting the plurality of spheres. One provides a coating on the bioprocessor surface area to expand cells, then attaches a protein to the coating, immobilizes biotinylated antibodies to the protein, thereafter flowing cells through the bioprocessor leading to the cells binding to the one or more biotinylated antibodies. Exposing the cells to a perfusion media containing a signaling molecule promotes cell expansion.

Figure 6:
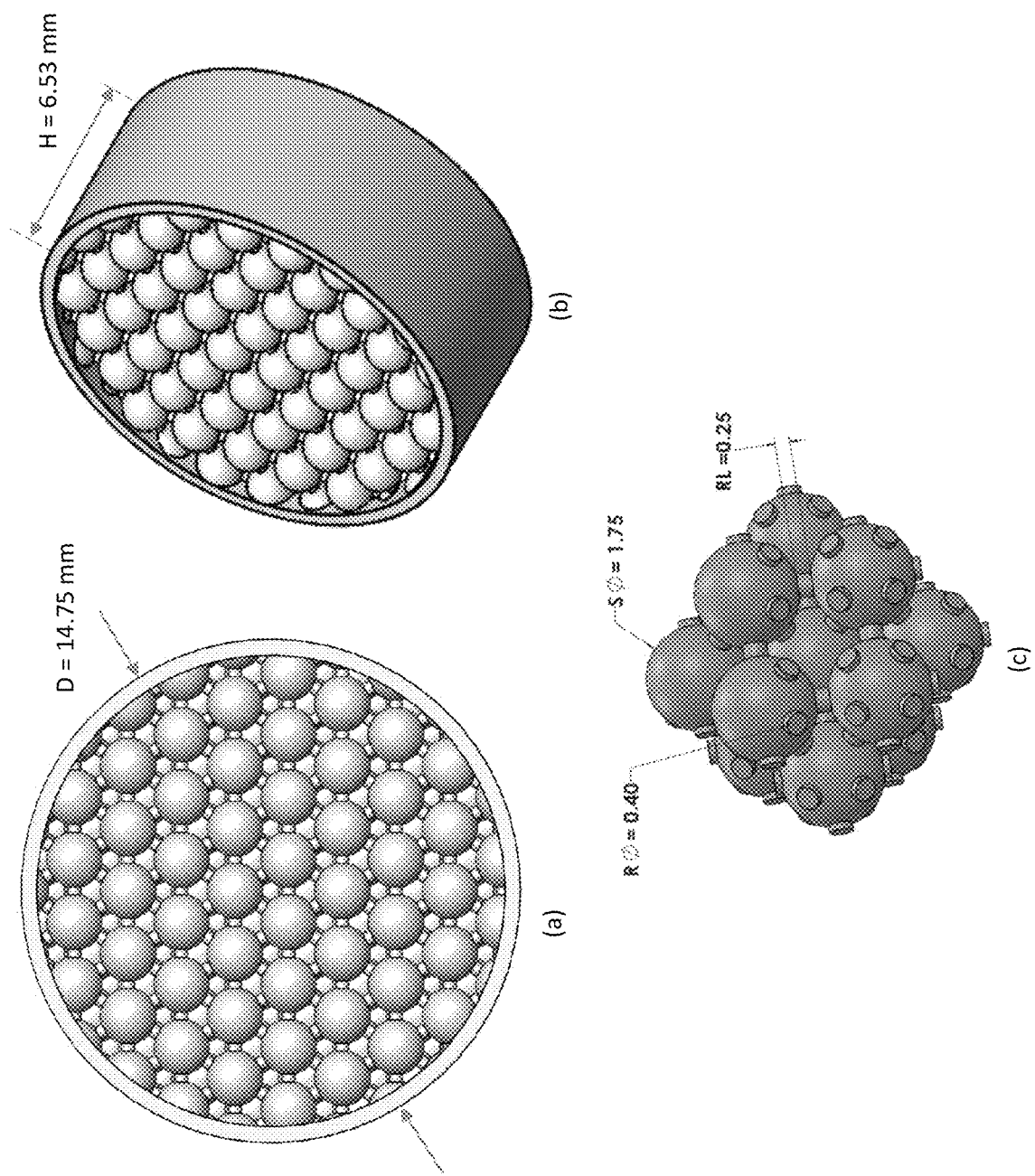
FIG. 6. Depicted is an example of 3D bioprocessor (a) & (b) This bioprocessor has an overall diameter D=14.75 mm, and height H=6.53 mm. (c) a sphere-rod unit has the sphere diameter $S\varphi=1.75$ mm, rod diameter $R\varphi=0.40$ mm, and the rod length RL=0.25 mm. The 3D bioprocess is composed of a large number of the sphere-rod units interconnected each other and tightly packed together in 3D space.

The dimension of the sphere-rod unit depends on the (1) diameter of the sphere (S$\varphi$), (2) the diameter of rod (R$\varphi$), and (3) the length of the rod (RL) as shown in FIG. 6. The diameter of the sphere (S$\varphi$) can range from about 25 μm to about 25 mm; the preferred range is from about 250 μm to about 6 mm. This includes spheres of about 2 mm. The diameter of rod (R$\varphi$) can range from about 12.5 μm to about 12.5 mm; the preferred range is from about 125 μm to about 3 mm. The rod length (RL) can range from about 0.1 μm to about 25 mm; the preferred range is from about 100 μm to about 3 mm. The change of sphere-rod dimension changes the surface-to-volume ratio of the 3D bioprocess. It is preferred that the diameter of the rod R$\varphi$ be less than half of sphere diameter, S$\varphi$. For example, sphere diameter, S$\varphi$, of about 1-3 mm, including sphere diameter, S$\varphi$, of about 2 mm, rod diameter, R$\varphi$ of about 125 μm to about 3 mm, rod length, RL, of about 100 μm to about 3 mm. It is preferred that the diameter of the rod R$\varphi$ be less than half of sphere diameter, S$\varphi$. In one example, FIG. 6 has the total surface area of 25.49 cm$^2$, and the volume of about 1 mL, which resulted the surface-to-volume ratio of 25.49 cm$^2$/mL.

In another method, T-cell expansion includes supplying a 3D bioprocessor with a plurality of spheres and a plurality of rods that interconnects the plurality of spheres, providing a coating on said bioprocessor surface area for cell expansion, attaching a protein attached to the coating, immobilizing one or more biotinylated antibodies to the protein, flowing T-cells through the bioprocessor having T-cell receptors, where activation occurs by T-cell receptors binding to the one or more biotinylated antibodies. Exposing the activated T-cells to a perfusion media containing a signaling molecule promotes T-cell expansion. The coating can be a protein coating, including a tetrameric protein such as avidin or streptavidin. Biotinylated antibody for use in the method includes anti-CD3 antibody, anti-CD28 antibody, and anti-CD2 antibody. Signaling molecules in the perfusion media include cytokine signaling molecules.

In another method, a mixed population of cells is flowed through the bioprocessor, with isolation of one or more cell types in the mixed population. This includes, for example, immunological cells, with isolation of T cell, NK cells, B cells by using antibodies specific these one or more cell types. Following isolation, each of the captured cell types in the bioprocessor can be expanded by, for example, culturing in the presence of an activation media with a signaling molecule, such as a cytokine. In other embodiments, cells, such as adherent cells, can be flowed through the bioprocessor to promote differentiation.

The 3D bioprocessor can be formed from a material that has a tensile modulus of at least 0.01 GPa. The 3D bioprocessor can be formed from a material that is biocompatible, including for example, a material not susceptible to hydrolysis during cell cultivation such that the amount of hydrolysis does not exceed 5.0% by weight of the material present.

The dimension of the sphere-rod unit depends on the (1) diameter of the sphere (S$\varphi$), (2) the diameter of rod (R$\varphi$), and (3) the length of the rod (RL) as shown in FIG. 6. The diameter of the sphere (S$\varphi$) can range from about 25 μm to about 25 mm; the preferred range is from about 250 μm to about 6 mm. This includes spheres of about 2 mm. The diameter of rod (R$\varphi$) can range from about 12.5 μm to about 12.5 mm; the preferred range is from about 125 μm to about 3 mm. The rod length (RL) can range from about 0.1 μm to about 25 mm; the preferred range is from about 100 μm to about 3 mm. The change of sphere-rod dimension changes the surface-to-volume ratio of the 3D bioprocess. It is preferred that the diameter of the rod R$\varphi$ be less than half of sphere diameter, S$\varphi$. In various configuration, one organizes the plurality of spheres and the plurality of rods in one or more layers. In other embodiments, the one or more layers includes at least two layers, with each layer offset from an adjacent layer. Spheres in the plurality of spheres can each be connected by 4, 5, 6, 7, 8 or more rods.

One can introduce T-cells into the bioprocessor applying a number cells at a flow rate, so as to impose a specific shear stress to maximize T-cell binding. One example includes shear stress range between 0.1 Pa to 1.2 Pa and a varying flow rate (0.06-6 ml/h).

One can scale the size of the underlying design so as to produce a certain number of cell of interest. For example, autologous therapy can require 5×10⁸ CAR T cells, with T cell expansion at about 60× times the number of input cells, and the percentage of T cells in patients' PBMC sample can range from 5% to 50%, a typical sample used as the input to the CAR T cell expansion process contains anywhere between 20 and 200×10⁶ PBMCs. Therefore, to activate T cells in 200×10⁶ PBMCs, a 3D bioprocessor with a surface area of 250 cm² is sufficient for autologous clinical application.

In other embodiments, the method is for isolating rare cell types from a population of cells. For example, the 3D bioprocessor includes a plurality of spheres with a plurality of rods interconnecting the plurality of spheres. One provides a coating on the bioprocessor surface area, and then attaches a protein to the coating, immobilizes biotinylated antibodies to the protein. The antibodies are target to bind one or several cell types. When a mixing types of cells flowing through the bioprocessor leading to a specific group of cells binding to the one or more biotinylated antibodies and retained in the bioreactor. The rest of cells flows out from the bioprocessor. The cells bound in the bioreactor are called deleted. The cells flow out of the bioprocessor are negatively selected. This is an example of using the bioprocess for cell separation, or isolation, or referred to as cell purification.

Described herein is a quantity of cells made by a method of supplying a 3D bioprocessor with a plurality of spheres and a plurality of rods interconnecting the plurality of spheres, thereafter providing a coating on the bioprocessor surface area, and then providing a protein attached to the coating. One can then provide one or more biotinylated antibodies immobilized on the protein, flowing cells through the bioprocessor, wherein the cells bind to the one or more biotinylated antibodies. The cells can be a mixed population of cells, with antibodies specific for one of the population of cells. Whereas certain cells will flow through and not be captured by the bioprocessor, antibodies specific for one of the population of cells will capture the population, which can be eluted for isolation, separation and further analysis.

Also described herein is a quantity of T cells made by the method of supplying a 3D bioprocessor with a plurality of spheres interconnected by a plurality of rods, providing a coating the bioprocessor surface area to expand cells, attaching a protein to the coating, immobilizing one or more biotinylated antibodies. This is followed by flowing T-cells through a bioprocessor having T-cell receptors, where the T-cell receptors bind to said one or more biotinylated antibodies and become activated. One can then expand the activated T-cells to a perfusion media containing a signaling molecule. Spheres in the plurality of spheres can each be connected by 4, 5, 6, 7, 8 or more rods.

A quantity of T cells for autologous therapy is about 2, 3, 4, or 5×10⁸ or more CAR T cells. T cell expansion can be about 20-30×, 30-40×, 40-50×, 50-60×, 60× or more of input cells, and with PBMC sample 5% to 50% including T cells, the method may require use of anywhere between 20 and 200×10⁶ PBMCs. For example, activating T cells in 200×10⁶ PBMCs, would suggest use of a 3D bioprocessor with a surface area of 250 cm² is sufficient for clinical application.

Further described herein is an apparatus that is a plurality of spheres interconnected by a plurality of rods. The diameter of the sphere (Sφ) can range from about 25 μm to about 25 mm; the preferred range is from about 250 μm to about 6 mm. This includes spheres of about 2 mm. The diameter of rod (Rφ) can range from about 12.5 μm to about 12.5 mm; the preferred range is from about 125 μm to about 3 mm. The rod length (RL) can range from about 0.1 μm to about 25 mm; the preferred range is from about 100 μm to about 3 mm. The change of sphere-rod dimension changes the surface-to-volume ratio of the 3D bioprocess. It is preferred that the diameter of the rod Rφ be less than half of sphere diameter, Sφ. In various configuration, one organizes the plurality of spheres and the plurality of rods in one or more layers. In other embodiments, the one or more layers includes at least two layers, with each layer offset from an adjacent layer. Spheres in the plurality of spheres can each be connected by 4, 5, 6, 7, 8 or more rods.

The apparatus can include a protein coating on the surface of the apparatus. One can attach one or more biotinylated antibodies to the protein coating, including for example, anti-CD3 antibody, anti-CD28 antibody, and anti-CD2 antibody.

The dimension of the sphere-rod unit depends on the (1) diameter of the sphere (Sφ), (2) the diameter of rod (Rφ), and (3) the length of the rod (RL). The diameter of the sphere (Sφ) can range from about 25 μm to about 25 mm; the preferred range is from about 250 μm to 6 mm. The diameter of rod (Rφ) can range from about 12.5 μm to about 12.5 mm; the preferred range is from about 125 μm to about 3 mm. The rod length (RL) can range from 0 to about 25 mm; the preferred range is from about 100 μm to about 3 mm.

For example, sphere diameter, Sφ, of from about 1 to about 3 mm, including sphere diameter, Sφ, of about 2 mm, rod diameter, Rφ of from about 125 μm to about 3 mm, rod length, RL, of from about 100 μm to about 3 mm. It is preferred that the diameter of the rod Rφ be less than half of sphere diameter, Sφ.

The change of sphere-rod dimension changes the surface-to-volume ratio of the 3D bioprocessor. Spheres in the plurality of spheres can each be connected by 4, 5, 6, 7, 8 or more rods. As described herein, a 3D bioprocess with a surface area of about 250 cm² is sufficient for certain clinical applications.

The bioprocessor may be made of biocompatible or bio-inert polymeric materials such as polystyrene, polycarbonate, acrylonitrile-butadiene-styrene (ABS), polylactic acid (PLA), polycaprolactone (PCL) used in FDM (fused deposition modeling) 3D printing technology. Reference to biocompatible or bio-inert should be understood as a material that is non-toxic to the culturing cells. In addition, the polymeric materials for the 3D bioprocessor are preferably selected from those polymers that at not susceptible to hydrolysis during cell cultivation, such that the amount of hydrolysis does not exceed 5.0% by weight of the polymeric material present, more preferably it does not exceed 2.5% by weight, and most preferably does not exceed 1.0% by weight. The bioprocessor may also be made of photopolymerization biocompatible materials (e.g., poly(methyl methacrylate) or PMMA, etc.) used in SLA (stereolithography) and DLP (digital light processing) 3D printing technologies.

Furthermore, the 3D bioprocessor herein is preferably one that is made from materials that have a tensile modulus of at least 0.01 GPa. More preferably, the Tensile Modulus has a value that is in the range of from about 0.01 to about 20.0 GPa, at 0.01 GPa increments. Even more preferably, the Tensile Modulus for the material for the 3D bioprocessor is in the range of from about 0.01 to about 10.0 GPa, or from about 1.0 to about 10 GPa. For example, with respect to the earlier referenced polymeric materials suitable for manufacture of the 3D bioprocessor herein, polystyrene indicates a tensile modulus of about 3.0 GPa, polycarbonate at about 2.6 GPa, ABS at about 2.3 GPa, PLA at about 3.5 GPa, PCL at about 1.2 GPa, and PMMA at about 3.0 GPa.

Other supporting information is found in U.S. Patent Publication No. US2019/0309250A1, which is fully incorporated by reference herein.

EXAMPLE 1

Sphere and Rod Design for the Cell Expansion

Figure 3:
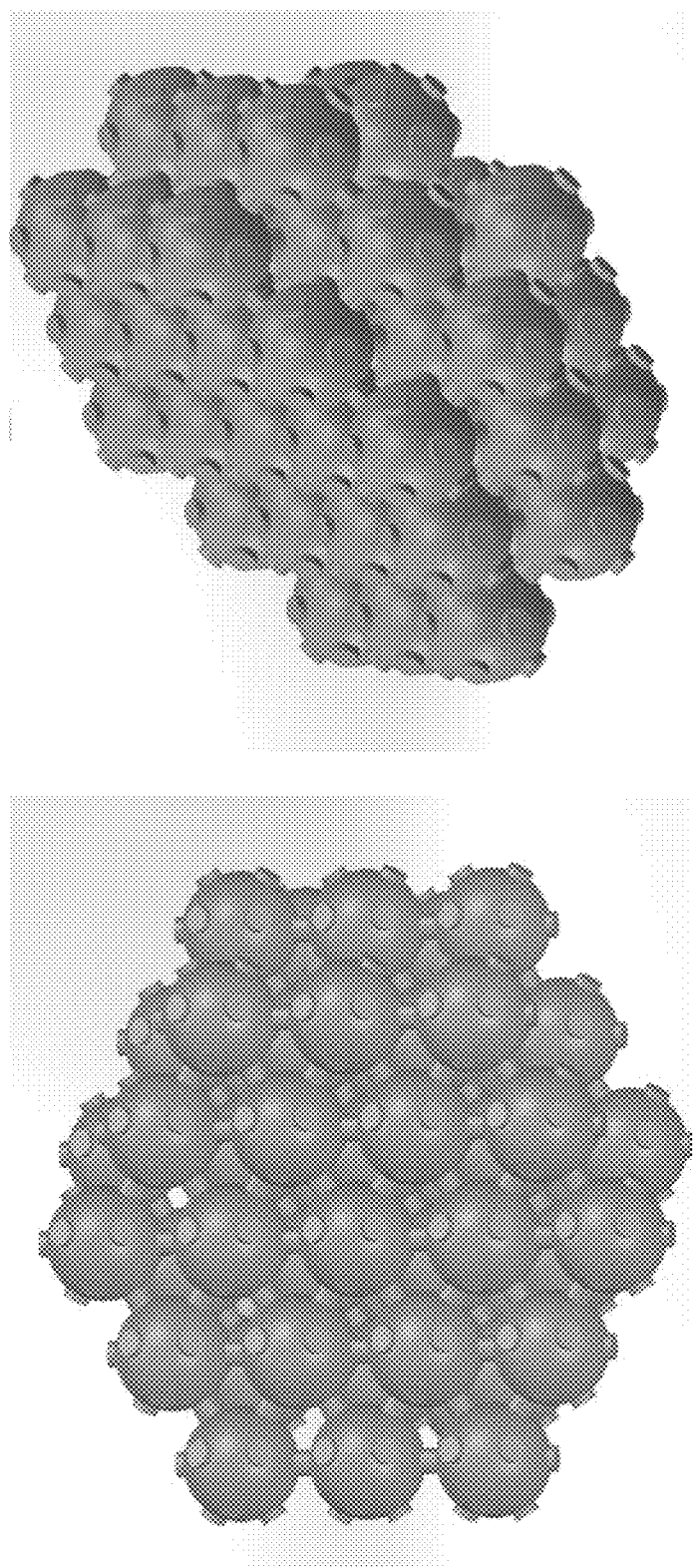
FIG. 3. Depicted is a unique structure of the 3D bioprocessor including spheres and interconnecting rods.
Figure 4:
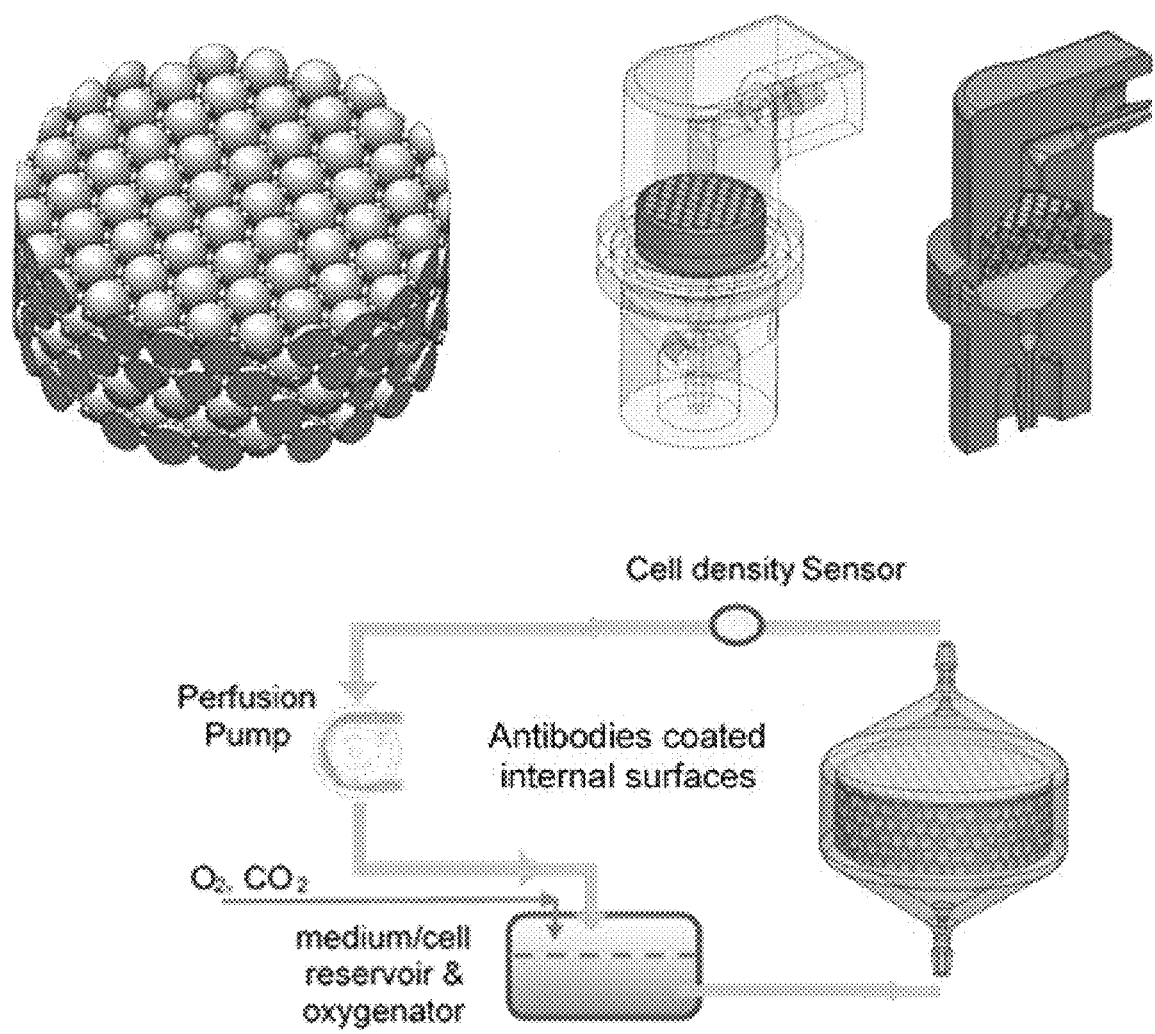
FIG. 4. Depicted is the 3D bioprocessor for use in a method as packed with an inlet and outlet to form a component in a perfusion flow system for cell processing.

The 3D bioprocessor is composed of spherical beads tightly arranged in 3D space with and interconnected with cylindrical rods as shown in FIG. 3. The space between the spherical beads allow fluid flow through. The 3D bioprocessor is composed of a large number of sphere-rod unit that is shown in FIG. 1(c). The interconnected sphere-rod units, tightly packed together, form a repeatable and non-random mesh structure, which has a large surface-to-volume ratio. The structure is enclosed by a wall that facilitates liquid perfuse through the mesh structure to deliver nutrition and oxygen to living organisms like cells.

The spherical beads with position offset layer-by-layer ensures that fluid flow over through all spherical beads surface, which significantly enhance the interaction between fluid and spherical beads. This structure, with some similar features as the pillar structure used in microchip technology to detect circulating tumor cells, has the potential to facilitate the isolation of cancer cells (an application of cell isolation), and any other targeting cells with the appropriated antibodies coating on the surface of the spherical beads. In addition to cell isolation, the bioprocessor has potential for T cell activation and transduction when the spherical beads surfaces are coated with antibodies like anti-CD3, CD28 to stimulate the T cells.

EXAMPLE 2

3-D Printed Structure

Figure 5:
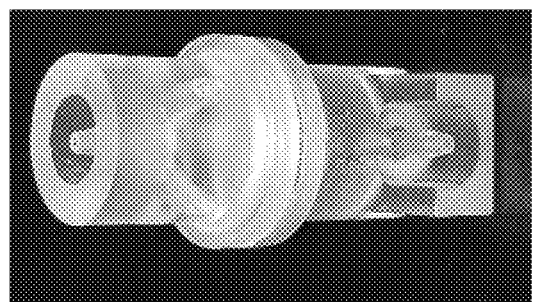
FIG. 5. Depicted is a 3D printed bioprocessor together with inlet and outlet structure to allow fluid flow through the bioprocessor.
Figure 5:
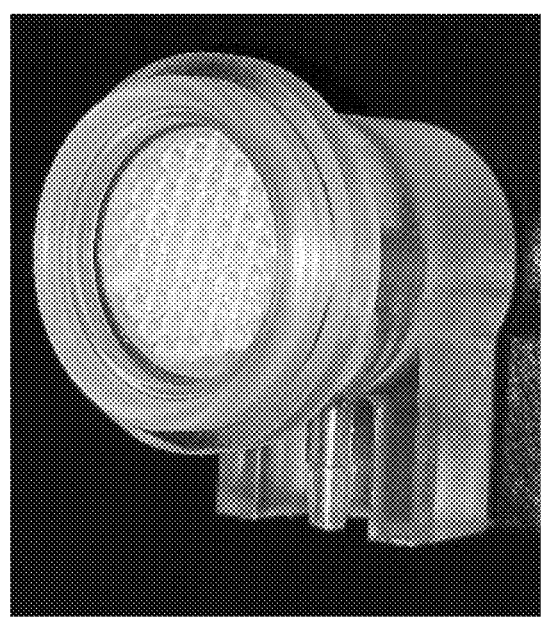
Figure 5:
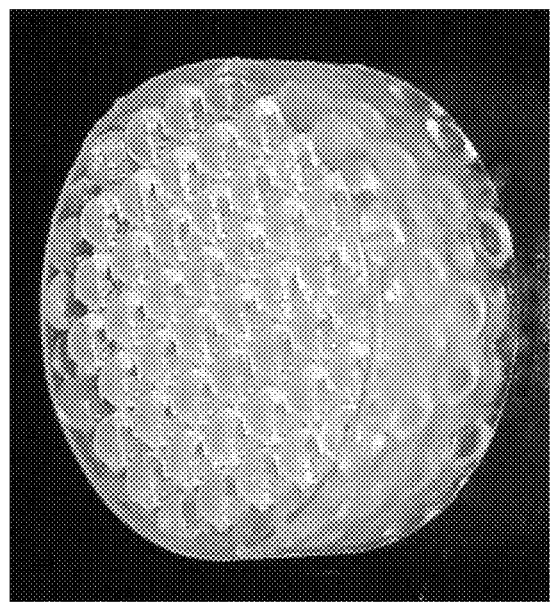

The novel 3D bioprocessor with its complex topology is difficult to fabricate with traditional injection-molding manufacturing process. The Inventors have developed a method of using additive manufacturing or 3D printing to precisely fabricate the structure shown in FIG. 5. The Inventors printed the bioprocessor using stereolithography (SLA), or digital light process (DLP) technology, which yielded bioreactors with a smoother surface than other 3D printing method.

EXAMPLE 3

3-D Printed Structure Details and Additional Information

An example of the 3D bioprocessor is illustrated in FIG. 6 with dimension of the sphere-rod unit depends on the 1) diameter of the sphere (S$\varphi$), 2) the diameter of rod (R$\varphi$), and the length of the rod (RL). The change of sphere-rod dimension changes the surface-to-volume ratio of the 3D bioprocess, with rod length increasing void space in the design and being a primary driver of design volume.

The example of the 3D bioprocessor in FIG. 6 has the total surface area of 25.49 cm$^2$, and the volume of about 1 mL, which resulted in the surface-to-volume ratio of 25.49 cm$^2$/mL.

EXAMPLE 4

Manufacture Scale—Clinical Use

If the surface of the bioprocess is immobilized with anti-CD3 antibodies, then the T cells perfusion through the 3D bioprocess can bind the anti-CD3 antibodies, and thus be activated. Using the 3D bioprocess illustrated in FIG. 6 as an example, the 25.49 cm$^2$ total surface area is approximately equivalent to the total surface area of 6.6×10$^7$ magnetic beads with the diameter of 3.5 μm. These number of magnetic beads can typically process about 2.2×10$^7$ of peripheral blood mononuclear cells (PBMCs) for T cell expansion. If the 3D bioprocess can immobilize similar density of antibodies on its internal surface, the 3D bioprocess is expected to process and equivalent number of PBMCs for T cell expansion.

A typical autologous CAR T cell therapy treatment needs approximately 5×10$^8$ CAR T cells. Considering the T cell expansion factor in the final step is usually ~60 times, and the percentage of T cells in patients' PBMC sample can range from 5% to 50%, a typical sample used as the input to the CAR T cell expansion process contains anywhere between 20 and 200×10$^6$ PBMCs. Therefore, to activate T cells in 200×10$^6$ PBMCs, a 3D bioprocess with a surface area of 250 cm$^2$ is sufficient for clinical application.

The Inventors have fabricated bioreactor with the internal surface of 25,000 cm$^2$, which may be suitable for allogenic CAR T cell therapy. Because of using 3D printing as the fabrication technique, the 3D bioprocess is easy to scale-up, scale-down, and scale-out for different applications.

EXAMPLE 5

Specific Advantages for CAR-T

Another feature of the 3D bioprocess is that it can control T cell interactions with the 3D bioprocess's internal surface when T cells perfuse through the structure. Unlike loose microbeads, whose internal structure is neither regular or uniform, the user can control parameters to achieve desirable interaction between cell and antibody coated surface.

A notable example is that the shear stress on T cells can be controlled by the perfusion flow rate. Several research groups have studied the effect of the volumetric flow rate and shear stress on cell attachment to surfaces. The study of CD8+ and CD4+ T-cells attachment to antigen-bearing dendritic cells indicates that a shear stress range between 0.1 Pa to 1.2 Pa and a varying flow rate (0.06-6 ml/h) resulted in maximum T-cell binding.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are apparatus designs, processes of using such designs, cells compatible with such apparatuses and, methods and compositions for production of such cells, including media formulations, related bioprocess techniques and other variations of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method, comprising:
supplying a 3D bioprocessor comprising a plurality of spheres and a plurality of rods interconnecting the plurality of spheres, the plurality of rods assisting in providing spacing between the plurality of spheres that are adjacent to each other;
providing a coating on a surface area of the 3D bioprocessor, the surface area including the plurality of spheres and the plurality of rods;
providing a protein attached to the coating;
providing one or more biotinylated antibodies immobilized on the protein;
flowing cells through the 3D bioprocessor, wherein the cells bind to the one or more biotinylated antibodies.

2. The method of claim 1, wherein the cells comprise T-cells, Wherein receptors of the T-cells bind to the one or more biotinylated antibodies and are activated and further comprising exposing the activated T-cells to a perfusion media containing a signaling molecule to promote T-cell expansion.

3. The method of claim 1, wherein the coating is a protein coating.

4. The method of claim 1, wherein the protein comprises a tetrameric protein.

5. The method of claim 4, wherein the tetrameric protein comprises avidin or streptavidin.

6. The method of claim 1, wherein the one or more biotinylated antibody is selected from the group consisting of: anti-CD3 antibody, anti-CD28 antibody, and anti-CD2 antibody.

7. The method of claim 2, wherein the signaling molecule comprises a cytokine signaling molecule.

8. The method of claim 1, wherein the 3D processor is formed from a material that has a Tensile Modulus of at least 0.01 GPa.

9. The method of claim 1, wherein the 3D bioprocessor is formed from a material that is biocompatible.

10. The method of claim 1, wherein the 3D bioprocessor is formed from a material not susceptible to hydrolysis during cell cultivation such that the amount of hydrolysis does not exceed 5.0% by weight of the material present.

11. The method of claim 1, wherein the diameter of the plurality of spheres is from about 10 µm to about 10 mm.

12. The method of claim 11 wherein the diameter of the plurality of spheres is from about 1 mm to about 3 mm.

13. The method of claim 1, wherein the length of the plurality of rods is from about 0.1 µm to about 10 mm.

14. The method of claim 13, wherein the length of the plurality of rods is from about 100 µm to about 3 mm.

15. The method of claim 1, wherein the plurality of spheres and the plurality of rods are organized in one or more layers.

16. The method of claim 15, wherein the one or more layers comprises at least two layers, with each layer offset from an adjacent layer.

17. The method of claim 1, wherein the plurality of spheres and the plurality of rods form a repeatable and non-random mesh structure.

18. The method of claim 1, wherein the plurality of spheres and the plurality of rods form a fixed structure of substantial uniformity.

19. The method of claim 1, wherein the 3D bioprocessor comprises a polymeric material selected from polystyrene, polycarbonate, acrylonitrile-butadiene-styrene (ABS), polylactic acid (PLA), and polycaprolactone (PCL).

20. The method of claim 1, wherein the 3D bioprocessor comprises a photo-polymerization biocompatible material.

21. The method of claim 20, wherein the photo-polymerization biocompatible material is poly(methyl methacrylate).

22. The method of claim 1, wherein the 3D bioprocessor comprises a material having a tensile modulus of from about 0.01 to about 10.0 GPa.

23. The method of claim 1, wherein each of the diameters of the plurality of rods is less than half of each of the diameters of the plurality of spheres.

24. A method, comprising;
supplying a 3D bioprocessor comprising a plurality of spherical beads and a plurality of rods interconnecting the plurality of spherical beads, the plurality of rods assisting in providing spacing between the plurality of spherical beads that are adjacent to each other;
providing a coating on a surface area of the 3D bioprocessor, the surface area including the plurality of spherical beads and the plurality of rods;
providing a protein attached to the coating;
providing one or more biotinylated antibodies immobilized on the protein;
flowing cells through the 3D bioprocessor, wherein the cells bind to the one or more biotinylated antibodies.

25. The method of claim 24, wherein the plurality of rods is cylindrical.

26. The method of claim 24, wherein the coating is a protein coating.

27. The method of claim 24, wherein the diameter of the plurality of spherical beads is from about t mm to about 3 mm.

28. The method of claim 24, wherein the plurality of spherical beads and the plurality of rods form a repeatable and non-random mesh structure.

29. The method of claim 24, wherein the plurality of spherical beads and the plurality of rods form a fixed structure of substantial uniformity.

30. The method of claim 24, wherein each of the diameters of the plurality of rods is less than half of each of the diameters of the plurality of spherical beads.

* * * * *

UNITED STATES PATENT AND TRADEMARK OFFICE
CERTIFICATE OF CORRECTION

PATENT NO. : 11,492,580 B2
APPLICATION NO. : 16/872823
DATED : November 8, 2022
INVENTOR(S) : Ling et al.

Page 1 of 1

It is certified that error appears in the above-identified patent and that said Letters Patent is hereby corrected as shown below:

In the Claims

At Column 13, Line 1 (Claim 8, Line 1), please delete "the 3D processor" and insert --the 3D bioprocessor-- therefor.

At Column 14, Line 26 (Claim 27, Line 2), please delete "about t mm" and insert --about 1 mm-- therefor.

Signed and Sealed this
Fifth Day of December, 2023

Katherine Kelly Vidal
*Director of the United States Patent and Trademark Office*